United States Patent [19]

Salkind

[11] 4,228,550
[45] Oct. 21, 1980

[54] DISTAL URINARY REPLACEMENT PROSTHESIS

[76] Inventor: Henry Salkind, 3415 Fifth Ave., Youngstown, Ohio 44505

[21] Appl. No.: 53,431

[22] Filed: Jun. 29, 1979

[51] Int. Cl.³ ............................................. A61F 1/24
[52] U.S. Cl. ......................................................... 3/1
[58] Field of Search ............... 3/1; 128/1 R, 294, 295, 128/DIG. 25

[56] References Cited

U.S. PATENT DOCUMENTS

| | | |
|---|---|---|
| 3,783,454 | 1/1974 | Sausse et al. ................................. 3/1 |
| 3,881,199 | 5/1975 | Treace ......................................... 3/1 |
| 3,953,897 | 5/1976 | Chevallet et al. ............................ 3/1 |
| 4,044,401 | 8/1977 | Guiset ......................................... 3/1 |

FOREIGN PATENT DOCUMENTS

| | | |
|---|---|---|
| 2714810 | 10/1977 | Fed. Rep. of Germany .................. 3/1 |
| 2116838 | 7/1972 | France .......................................... 3/1 |

OTHER PUBLICATIONS

"Bladder Regeneration After Cystectomy and Prosthetic Urinary Bladder Replacement" by T. H. Stanley et al., Transactions American Society for Artificial Internal Organs, vol. XVII, 1971, pp. 134–137.

Primary Examiner—Ronald L. Frinks
Attorney, Agent, or Firm—Webster B. Harpman

[57] ABSTRACT

An implant prosthesis for surgically by-passing the distal portion of the natural urethral tract for the removal of biological liquids, especially urine, consists of one or more artificial ureters disposed in a conical sheath connected with flexible tubing joining a tank forming a bladder replacement which in turn is connected by flexible tubing to the urethra when retained or extends to provide a controlled valved vent at the surface of a patient's body in which the prosthesis is surgically implanted, as for example following the removal of bladder cancer and its associated damaged distal urinary system.

13 Claims, 7 Drawing Figures

U.S. Patent  Oct. 21, 1980  4,228,550
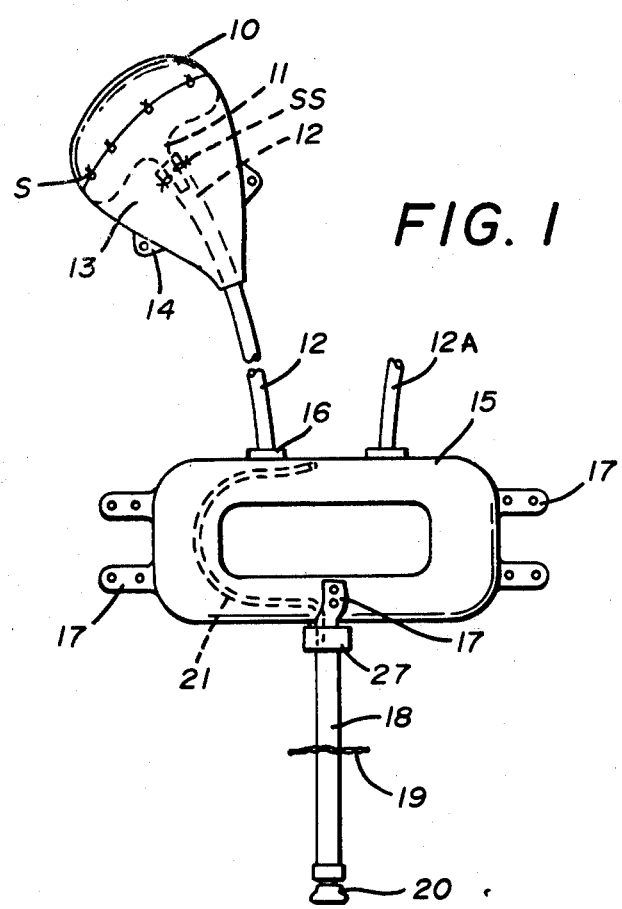
FIG. 1
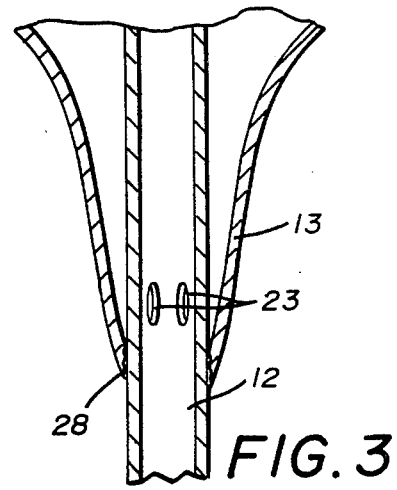
FIG. 3
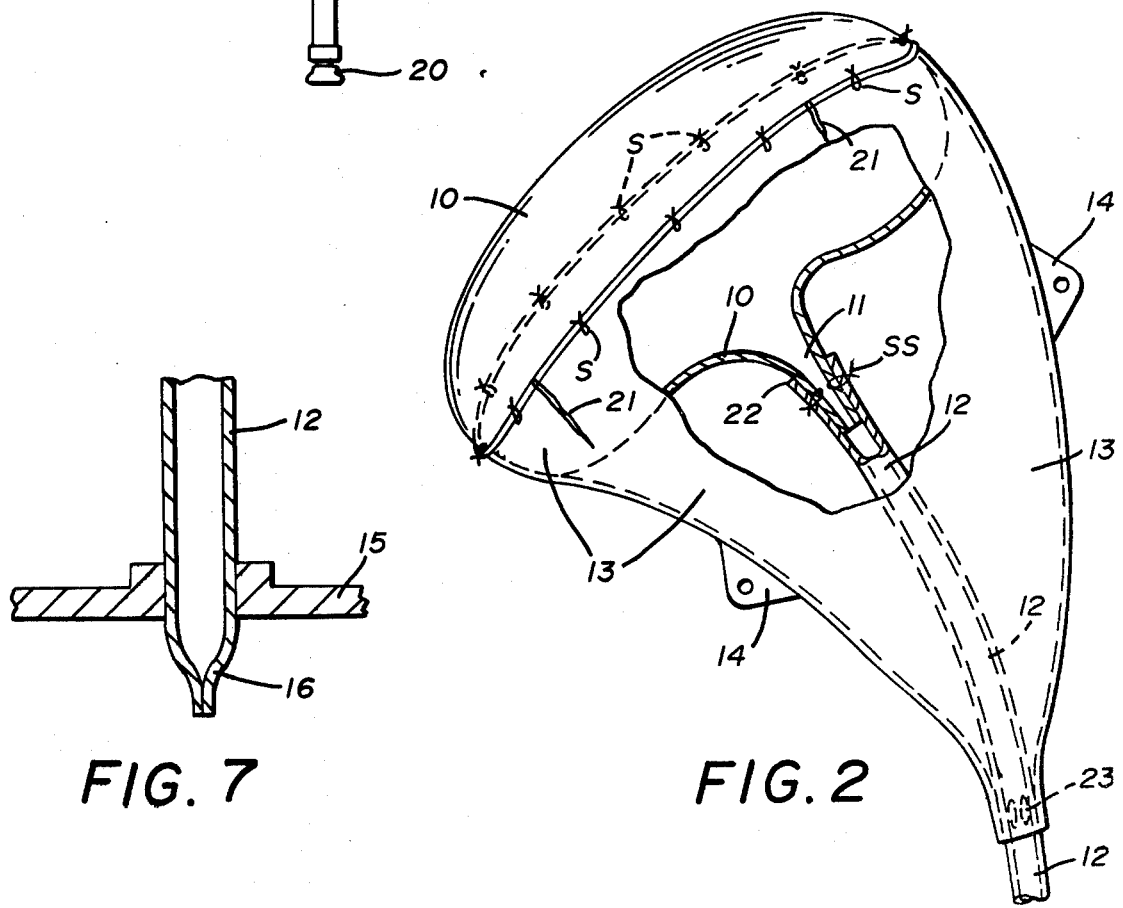
FIG. 7
FIG. 2

DISTAL URINARY REPLACEMENT PROSTHESIS

BACKGROUND OF THE INVENTION (1) Field of the Invention:

This invention relates to the field of surgical implants and is particularly directed toward the implant of a distal urinary replacement prosthesis in a human patient.

(2) Description of the Prior Art:

The distal urinary replacement prosthesis disclosed herein is believed to be totally new as an acceptable solution involving replacement in such entities as extrophy of the bladder and trauma and other circumstances which make the urethra and/or bladder non-functioning.

Urethral shunt tube implants have been proposed for veterinary use as seen in U.S. Pat. No. 3,881,199 wherein a tubular implant replaces a portion of the natural urethral tract.

An implantable prosthetic duct arranged for connection to a ureter at one end and to a bladder at the other end is disclosed in U.S. Pat. No. 3,783,454. The distal urinary replacement prosthesis disclosed herein replaces the ureters, bladder, and urethra and its extension to and beyond the surface of the patient's body when necessary and provides a fail safe cystostomy area by making available anterosuperiorly in the collecting tank or replacement bladder in the case of emergency. Additionally localization of sites of future pathology within the prosthesis are aided by radiographic markers throughout and the prosthesis is devised and constructed so that in the event of a defect various portions of the prosthesis may be substituted without requiring total withdrawal of the prosthesis. Additionally the junction of the renal pelvis or ureter with the prosthetic ureter, provides a fail safe arrangement in the event of any distal slough on the part of the human tissue by reason of the impermeable sleeve which encompasses the circumference of the kidney so that any and all leakage is confined within the prosthesis for distal funneling. Versatility of the prosthesis in replacement in those individuals with congenital anomalies are quite feasible since interchangeable parts of the prosthesis make it feasible to add additional sections such as ureters and make it possible to convert the prosthesis to a unilateral functioning kidney and ureter.

SUMMARY OF THE INVENTION

The distal urinary replacement prosthesis disclosed herein replaces the ureters, bladder and urethra when deemed necessary for medical reasons. All affected human tissue is surgically removed including the ureters from just below the renal pelvis, the bladder and the urethra are also removed so that all possible disease affected portions of the body are removed thereby providing a minimal risk to the lingering medical complications. The prosthesis consists of one or more artificial ureters attached to the renal pelvis of the kidney, a sheath positioned about the kidney and engaged on the artificial ureter for cooperating drainage into the ureter and the ureter is placed in communication with a tank or bladder replacement which is arranged for skeletal support in the body of the patient. A flexible tube, including a vent tube, establishes communication between the tank or bladder replacement and the natural urethra, if it remains or is extended through the surface of the patient's body and provided with a controlled valve and vent opening.

DESCRIPTION OF THE DRAWINGS

FIG. 1 is a diagrammatic illustration of the distal urinary replacement prosthesis with parts broken away;

FIG. 2 is an enlarged detail of a portion of the prosthesis shown in FIG. 1 with parts broken away and parts in cross section;

FIG. 3 is an enlarged detail of a portion of the prosthesis shown in FIG. 2 with parts in cross section;

FIG. 7 is a cross sectional detail of a check valve which is preferably positioned between the artificial ureter and its point of connection with the tank or bladder replacement of the prosthesis.

DESCRIPTION OF THE PREFERRED EMBODIMENT

Figure 4:
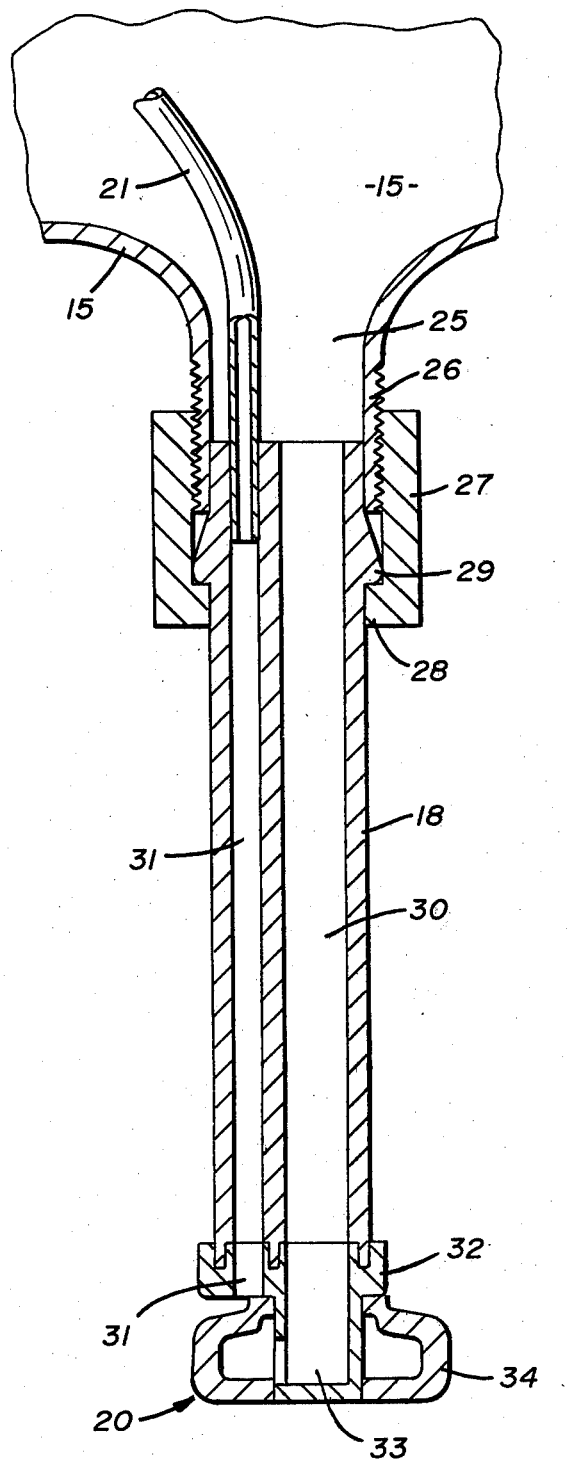
FIG. 4 is an enlarged vertical section of a portion of the prosthesis seen in FIG. 1.

By referring to the drawings and FIG. 1 in particular, it will be seen that a distal urinary replacement prosthesis has been disclosed in which a kidney 10 is illustrated as having one of its ureters 11 positioned in and attached to the upper end of an artificial ureter 12. A funnel-like sheath 13 is secured to the artificial ureter 12 at a location thereon spaced with respect to the end thereof engaging the ureter and renal pelvis 11 and tabs 14 on the sheath 13 enable the sheath to be attached to the skeletal or other body structure to properly locate the prosthesis in the body cavity as will be understood by those skilled in the art. The extending portion of the artificial ureter 12 communicates at its opposite end with a tank 15 which comprises a bladder replacement and the connection is preferably by way of a check valve 16. The artificial ureter 12 is surgically attached to the ureter or renal pelvis by sutures SS as is the upper open end of the funnel-like sheath 13, the sutures joining the sheath to the kidney. Those skilled in the art will observe that as illustrated in FIG. 1 a single kidney 10 is illustrated as connected with the distal urinary replacement prosthesis and it is obvious that the other kidney in the normal human is similarly connected with similar devices, not shown, by way of a second artificial ureter 12A to the tank 15 which forms the bladder replacement of the prosthesis. The tank 15 is provided with secondary tabs 17 so that the same may be sutured or otherwise attached to the skeletal or other body structure to assure the relative position of the tank portion of the prosthesis in the body cavity. A discharge flexible tube 18 communicates with the tank 15 and extends to the normal remaining urethra when present and is secured thereto as by suturing or when the normal urethra is removed the discharge flexible tube 18 is extended outwardly of the patient's body and attached to the opening by a suitable apertured patch 19 compatible with the body tissue and as will be understood by those skilled in the art. The outermost end of the flexible discharge tube 18 is provided with a combined vent and valve generally indicated at 20.

Still referring to FIG. 1 of the drawings, it will be seen that a representation of a plurality of sutures S have been illustrated where the upper open end of the conical sheath 13 is attached to the kidney 10. Similarly sutures SS are illustrated where the upper open end of the artificial ureter 12 is attached to the normal ureter or the renal pelvis 11.

In FIG. 1 of the drawings, broken lines indicate the presence of a flexible vent tube 21 which extends from a location in the uppermost portion of the tank 15 which is the bladder replacement and communicates with a passageway formed in the flexible tube 18 heretofore referred to and hereinafter described in greater detail.

In order that the prosthesis can be tailored by the surgeon installing the same in a patient, the portions thereof which are attached to the kidney or kidneys and the normal ureters or renal pelvis thereof have been arranged so that they can be adjusted as to size when attached thereto by the sutures or otherwise.

By referring now to FIG. 2 of the drawings an enlarged detail of the sheath 13 and its relation to the kidney 10 and and a ureter and/or the renal pelvis 11 may be seen and it will be observed that the outer annular enlarged end of the funnel-like sheath 13 is positioned around the kidney 10 and secured thereto by the sutures S. Slits 21 are formed in the sheath 13 which itself is made of thin polyvinyl or equivalent material, the slits 21 being appropriately located to permit clearance around the renal blood vessels and additionally facilitate the adjustment of the open upper end of the sheath 13 to the particular size and shape of the kidney 10 to which it is sutured as hereinbefore described.

Still referring to FIG. 2 of the drawings, it will be observed that the upper end of the artificial ureter 12 is enlarged as at 22. The artificial ureter 12 and particularly its upper end 22 can be provided in various sizes to accommodate anatomical variations. The enlarged upper end 22 is preferably made of knitted polyester fabric or equivalent material to permit adequate and effective suturing as at SS to the renal pelvis 11 or that portion of the normal ureter that remains.

Figure 6:
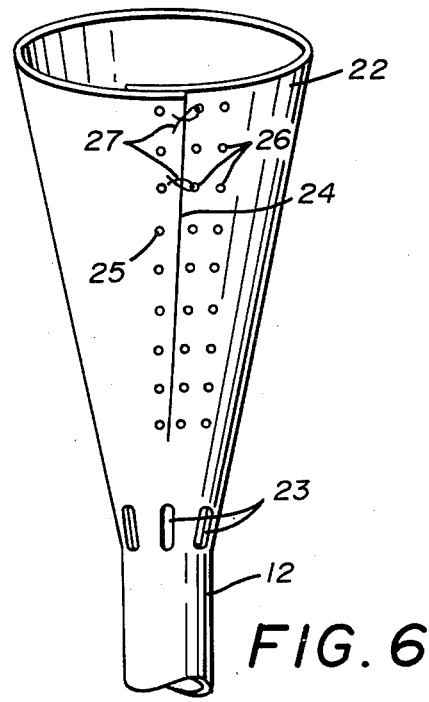
FIG. 6 is an enlarged detail of a portion of the prosthesis seen in FIG. 2 of the drawings.

The artificial ureter 12 and its enlarged upper end 22 may be seen in enlarged detail in FIG. 6 of the drawings and by referring thereto it will be oserved that several openings 23 are formed therein and that the enlarged upper portion 22 is slit axially as at 24 and the material overlapped. A series of studs 25 are arranged in a row along one side of the slit 24 and several registering rows of apertures 26 are formed in the enlarged upper end 22 of the artificial ureter 12 so that the effective size of the enlarged upper end 22 can be readily adjusted and secured by the surgeon at the time of the implant. These mechanical fasteners may also be secured by additional sutures applied by the surgeon as will be understood by those skilled in the art. One such suture is illustrated in FIG. 6 and indicated by the numeral 27.

By referring to FIG. 3 of the drawings, the portion of the artificial ureter 12 where it joins the lowermost and smallest diameter portion of the sheath 13 may be seen and the location of the openings 23 heretofore referred to as being formed in the artificial ureter 12 will be observed to be positioned above a line of attachment 28 where the lower end of the funnel-shaped sheath 13 is cemented or similarly affixed to the exterior of the artificial ureter which takes the form of a flexible tube at this point.

The openings 23 permit accumulated liquid in the case of leaks or failure at the connection of the artificial ureter to the renal pelvis to enter the artificial ureter and thus reach the tank 15.

In FIG. 7, an enlarged cross sectional elevation of the fitting joining the lower end of the artificial ureter 12 to the tank 15 may be seen and it will be observed that a check valve 16 is incorporated with the fitting which will prevent flow of liquid from the tank 15 into the artificial ureter 12 while permitting flow of liquid from the artificial ureter 12 into the tank 15.

By referring now to FIG. 4 of the drawings, a portion of the tank 15 may be seen in enlarged detail and it will be observed that the lower portion has a drain passageway 25 therein defined by a tubular member 26 which is exteriorly threaded. A flanged nut 27 is engaged on the tubular member 26 with its flange which is inturned at 28 underlying an annular shoulder 29 on the exterior of the upper end portion of the flexible discharge tube 18. The discharge tube 18 has two parallel passageways therein, the first and larger of these passageways in indicated by the numeral 30 and forms the liquid drain conduit. The second and smaller passageway defines an air vent 31. The upper end of the liquid drain passageway 30 communicates with the interior of the tank 15 and the upper end of the air vent passageway 31 communicates with the vent tube 21, which as hereinbefore described extends upwardly through the tank 15 to a point near its uppermost interior portion. The construction illustrated and herein described provides for the ready assembly of the several parts of the distal urinary replacement prosthesis which is convenient to the surgeon making the implant in the patient.

Figure 5:
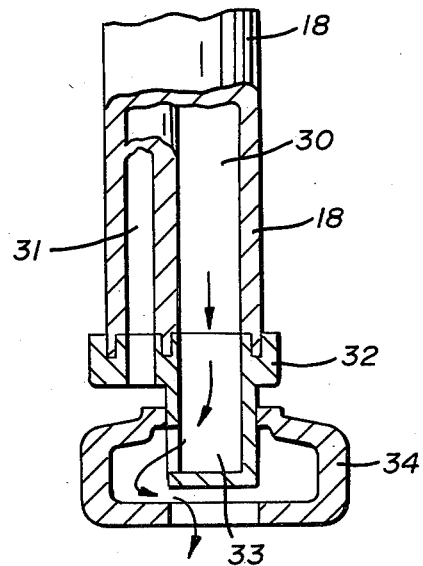
FIG. 5 is a detail of a portion of the device seen in FIG. 4 and illustrating a valved vent in open position.

Still referring to FIG. 4 of the drawings, it will be seen that the lower end of the flexible discharge tube 18 is provided with a fitting 32 which provides an opening to the atmosphere for the air vent passageway 31 and it extends the liquid drainage passageway 30 therebelow to form a side vented chamber 33. A manually movable closure or valve 34 is positioned thereon and is movable from the position shown in FIG. 4 where it forms a closure with respect to the chamber 33 to a position as shown in FIG. 5 of the drawings where the closure element 34 has been moved downwardly so as to open the side vented passageway in the chamber 33.

It will thus be seen that the distal urinary replacement prosthesis disclosed herein replaces the ureters, bladder and urethra when deemed necessary for medical reasons and that prosthesis is implanted by the surgeon after all affected human tissue is surgically removed including the ureters from just below the renal pelvis, the bladder and the urethra, etc. The prosthesis thus enables all possible disease affected portions of the body to be removed providing a minimal risk to lingering medical complications. When implanted by the surgeon, one or both of the kidneys are connected to the prosthesis as hereinbefore described and the arrangement is such that a fail safe connection is provided due to the dual function of the funnel-like sheath 13 and the artificial ureter 12. The urine discharged by the kidney or kidneys as the case may be, thus flows through the artificial ureters 12 and/or 12A into the tank 15 which replaces the bladder and is discharged from the tank 15 through the flexible discharge tubular member 18 which provides for the liquid discharge as well as providing an air vent as necessary to permit the liquid to flow from the tank 15. The tank 15 is collapsible upon itself as liquid drains therefrom. The flexible discharge and vent tubular member 18 extends outwardly of the patient's body cavity in which the prosthesis is implanted and provides a simple and readily controllable venting valve.

It will be observed that the prosthesis is so constructed that the level of attachment to the renal pelvis or distal ureter is facilitated by the simple tailoring of the prosthesis to fit the situation at the time of the operation and it will be further observed that the potential exists that the plastic material utilized in the formation of the prosthesis is strong enough to withstand the pressure of residual tumor encroachment if such should occur. The prosthesis is additionally X-ray coded and banded so that radiation therapy will not unfavorably alter the prosthesis, but would permit heavy radiation to be applied with the prosthesis in place for residual tumor treatment if such remains.

The formation of the prosthesis from several parts enables instrumentation capabilities to observe the inner aspects of the several areas of the prosthesis with capabilities for the correction of pathologies that may arise in the form of calculi, encrustations or other obstructions. In addition fail safe cystostomy area is made available anterosuperiorly in the collecting tank 15 in case of emergency by simple technique and localization of sites of future pathology within the prosthesis are aided by the radiographic markers throughout so that radiographic evaluation is possible. The formation of the prosthesis from several parts enable replacement of the parts without requiring total withdrawal of the prosthesis. The form and arrangement of the prosthesis makes possible versatility in replacement in those individuals with congenital anomalies since the interchangeable parts of the prosthesis permit the addition of additional ureters or the conversion of the prosthesis to a unilateral functioning kidney and ureter, all as will occur to those skilled in the art.

The sutures heretofore referred to may comprise any suitable suture material, one such material being urological 3/0 surgical silk. The cone-shaped sheath 13, the artificial ureter 12, the tank 15 which forms the replacement bladder and the discharge flexible tube 18 may be formed of any substance which is compatible with and resistant to attack by body fluids, specifically materials hereinbefore mentioned or any comparable, such as Silastic or a silicone elastomer. The upper end portion of the artificial ureter 12 has been described as being formed of a suitable mesh fabric such as polyethylene terephthalate which is sold commercially under the trademark Dacron. Additionally, polymerized tetrafluoroethylene may be used. The portions of the prosthesis which are cemented to one another may be secured by any adhesive which is compatable with and resistant to attack by body fluids, such as a well known medical grade silicone adhesive. The cone-shaped sheath 13 and flexible tubular replacement ureter 12 can be sufficiently porous to allow tissue cellular colonization thereinto.

It will thus occur to those skilled in the art that a distal urinary replacement prosthesis has been disclosed which may be effectively used in the replacement of ureters, bladder, and urethra damaged or destroyed by bladder cancer or wherein replacement is necessary due to other circumstances which may make the urethra and/or bladder non-functioning.

Although but one embodiment of the present invention has been illustrated and described, it will be apparent to those skilled in the art that various changes and modifications may be made therein without departing from the spirit of the invention and having thus described my invention, what I claim is:

1. A surgically implantable distal urinary replacement prosthesis for the collection and removal of urine from at least one kidney in a patient's body and comprising at least one flexible cone-shaped sheath having a first open end arranged for engagement about and attachment to at least a portion of said kidney so as to enclose the renal pelvis area thereof, a second end of said cone-shaped sheath being spaced from said renal pelvis area, a flexible tubular replacement ureter positioned partially within said cone-shaped sheath and extending outwardly thereof through said second end thereof and attached thereto in sealing relation, an end of said flexible tubular replacement ureter located within said cone-shaped sheath and arranged for engagement over a ureter in said renal pelvis area and adapted to be attached thereto, openings in said flexible tubular replacement ureter within said flexible cone-shaped sheath so that liquid within said flexible cone-shaped sheath can flow into said tubular replacement ureter, a tank forming a replacement bladder, said tubular replacement ureter being in communication with said tank and a flexible tubular member communicating with said tank and forming a discharge passageway extending therefrom.

2. The prosthesis set forth in claim 1 and wherein said cone-shaped sheath and said flexible tubular replacement ureter are sufficiently porous to allow tissue cellular colonization thereinto.

3. The prosthesis set forth in claim 1 and wherein a valve is incorporated in the flexible tubular replacement ureter at its point of communication with said tank forming the replacement bladder, said valve arranged to permit the flow of fluid from said ureter into said tank and to prevent the flow of fluid from said tank into said ureter.

4. The prosthesis set forth in claim 1 and wherein said flexible cone-shaped sheath is formed of a material that may be split to provide passageways for blood vessels and an adjustment of size with respect to registration with said kidney.

5. The prosthesis set forth in claim 1 and wherein the end of said flexible tubular replacement ureter positioned within said cone-shaped sheath is progressively enlarged toward its open end and split longitudinally through said enlarged area and fastening configurations are formed on either side of said split whereby the diameter of the enlarged end may be adjusted and secured in adjusted relation when engaged over a portion of a natural ureter in said renal pelvis area.

6. The prosthesis set forth in claim 1 and wherein the flexible tubular member communicating with the tank and forming a discharge passageway extending therefrom defines two tubular passageways, a flexible tube communicating with one of said passageways and extending into said tank to form an air vent.

7. The prosthesis set forth in claim 1 and wherein the flexible tubular member communicating with the tank and forming a discharge passageway extending therefrom defines two tubular passageways, a flexible tube communicating with one of said passageways and extending into said tank to form an air vent and wherein a manually movable valve element is attached to the end of the flexible tubular member in oppositely disposed relation to said tank.

8. The prosthesis set forth in claim 1 and wherein the cone-shaped sheath, the flexible tubular replacement ureter, the tank forming the bladder replacement and the flexible tubular member communicating with the tank and forming a discharge passageway are separately formed portions of the prosthesis and joined to one another by separable connections.

9. The prosthesis set forth in claim 1 and wherein the several sections thereof are X-ray coded and banded for visual X-ray examination.

10. The prosthesis set forth in claim 1 and wherein radiographic markers are incorporated in the prosthesis.

11. The prosthesis set forth in claim 1 and wherein the cone-shaped sheath is of a size and shape for encompassing the circumference of said kidney whereby any and all leakage would be within said sheath.

12. The prosthesis set forth in claim 1 wherein several apertured tabs are formed on said cone-shaped sheath and on said tank and arranged to provide members attachable to portions of said patient's body for supporting said sheath and tank in operative relation to said kidney.

13. The prosthesis set forth in claim 1 and wherein said tank is collapsible upon itself as liquid drains therefrom.

* * * * *